(12) United States Patent
Alanine et al.

(10) Patent No.: US 6,310,213 B1
(45) Date of Patent: Oct. 30, 2001

(54) ETHANESULFONYL-PIPERIDINE DERIVATIVES

(75) Inventors: Alexander Alanine, Riedisheim; Serge Burner, Durmenach-Ferrette, both of (FR); Bernd Büttelmann, Schopfheim (DE); Marie-Paule Heitz Neidhart, Hagenthal le Bas (FR); Georg Jaeschke, Basle (CH); Emmanuel Pinard, Linsdorf (FR); René Wyler, Zürich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/585,755

(22) Filed: Jun. 2, 2000

(30) Foreign Application Priority Data

Jun. 8, 1999 (EP) .................................................. 99111126

(51) Int. Cl.⁷ ...................... C07D 211/20; C07D 211/40; C07D 211/54
(52) U.S. Cl. ............................ 546/216; 546/219; 546/236
(58) Field of Search ...................... 546/216, 219, 546/236

(56) References Cited

FOREIGN PATENT DOCUMENTS

| 824098 | 2/1998 | (EP) | ...................................... 546/216 |
|---|---|---|---|
| WO 95/25721 | 9/1995 | (WO) | ...................................... 546/216 |
| WO 97/23216 | 7/1997 | (WO) | ...................................... 546/216 |

*Primary Examiner*—Alan L. Rotman
*Assistant Examiner*—Raymond Covington
(74) *Attorney, Agent, or Firm*—George W. Johnston; William H. Epstein

(57) ABSTRACT

The invention relates to compounds of the general formula

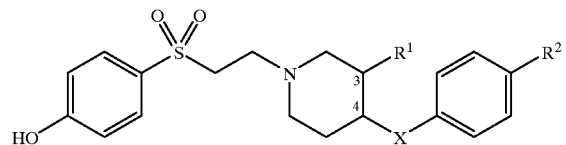

wherein
$R^1$ signifies hydrogen or hydroxy; $R^2$ signifies hydrogen or methyl; and X signifies —O— or —CH$_2$— and their pharmaceutically acceptable acid addition salts.

It has been shown that these compounds have a good affinity to the NMDA receptor and they are therefore useful in the treatment of diseases, wherein the therapeutic indications include acute forms of neurodegeneration caused, e.g., by stroke or brain trauma; chronic forms of neurodegeneration such as Alzheimer's disease, Parkinson's disease, Huntington's disease or ALS (amyotrophic lateral sclerosis); neurodegeneration associated with bacterial or viral infections, and, diseases such as schizophrenia, anxiety, depression and chronic/acute pain.

16 Claims, No Drawings

ETHANESULFONYL-PIPERIDINE DERIVATIVES

BACKGROUND OF THE INVENTION

Under pathological conditions of acute and chronic forms of neurodegeneration overactivation of NMDA receptors is a key event for triggering neuronal cell death. NMDA receptors are composed of members from two subunit families, namely NR-1 (8 different splice variants) and NR-2 (A to D) originating from different genes. Members from the two subunit families show a distinct distribution in different brain areas. Heteromeric combinations of NR-1 members with different NR-2 subunits result in NMDA receptors, displaying different pharmacological properties. Possible therapeutic indications for NMDA receptor subtype specific blockers include acute forms of neurodegeneration caused, e.g., by stroke or brain trauma; chronic forms of neurodegeneration such as Alzheimer's disease, Parkinson's disease, Huntington's disease or ALS (amyotrophic lateral sclerosis); neurodegeneration associated with bacterial or viral infections, diseases such as schizophrenia, anxiety and depression and acute/chronic pain.

Compounds of formula I and their salts are generically, but not specifically, known compounds, described in WO 95/25721. They are described to possess activities on the glutamate receptor or AMPA receptor for the treatment of diseases which are related to these receptors. Furthermore similar compounds are described in EP 824 098, in which the piperidine ring is substituted by a hydroxy group in 4-position. These compounds are described as possessing activity with regard to the NMDA receptor and are useful in the treatment of acute forms of neurodegeneration caused, for example, by stroke and brain trauma, and chronic forms of neurodegeneration such as Alzheimer's disease, Parkinson's disease, ALS (amyotrophic lateral sclerosis), neurodegeneration associated with bacterial or viral infections and acute/chronic pain.

It is known from EP 824 098 that these compounds are good NMDA receptor subtype specific blockers with a high affinity for NR2B subunit containing receptors and low affinity for NR2A subunit containing receptors. Activity versus $\alpha_1$-adrenergic receptors is also low and the compounds are active in vivo against audiogenic seizures in mice in the low mg/kg range. Importantly, these compounds are neuroprotective in an animal stroke model, namely, a permanent occlusion of the middle cerebral artery. However, in vitro and in vivo cardiotoxicity studies show that these compounds have the propensity to prolong cardiac action potential duration in vitro and consequently the 'QT'-interval in vivo and thus, have the potential to produce cardiac arrhythmias. The ability of such compounds to prolong the cardiac action potential was identified as being due to an action at the nERG potassium type channel, which is important for action potential repolarisation in humans and other species, and most compounds known to prolong the QT-interval in man are active at blocking this channel. Thus, the compounds of the prior art block recombinant human ERG potassium channels heterologously.

The compounds of the present invention are NMDA (N-methyl-D-aspartate)-receptor-subtype selective blockers. NMDA receptors have a key function in modulating neuronal activity and plasticity which makes them key players in mediating processes underlying development of CNS including learning and memory formation and function. However when overactive, NMDA receptors contribute to neurodegeneration. Therefore compounds which block NMDA receptor activation without undesirable side effects are therapeutically important.

SUMMARY OF THE INVENTION

The present invention relates to compounds of the general formula

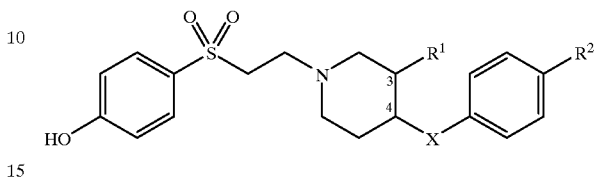

wherein
R$^1$ signifies hydrogen or hydroxy;
R$^2$ signifies hydrogen or methyl; and
X signifies —O— or —CH$_2$—
and to their pharmaceutically acceptable acid addition salts.

It has now surprisingly been found that the compounds of formula I are NMDA NR2B subtype selective antagonists whilst they share the highly specific subtype selective blocking properties compounds of the prior art, for example of 1-[2-(4-hydroxy-phenoxy)-ethyl]-4-(4-methyl-benzyl)-piperidin-4-ol (9), and are neuroprotectants. They are less active as blockers of the hERG potassium channels and, thus, are much less likely to have pro-arrhythmic activity in man. In view of their activity as NMDA receptor blockers, compounds of this invention are useful in treating neurodegeneration caused by NMDA receptor overactivity while avoiding pro-arrhythmic activity.

Objects of the present invention are novel compounds of formula I, the use in the treatment or prophylaxis of diseases caused by overactivation of respective NMDA receptor subtypes, which include acute forms of neurodegeneration caused, e.g., by stroke or brain trauma; chronic forms of neurodegeneration such as Alzheimer's disease, Parkinson's disease, Huntington's disease or ALS (amyotrophic lateral sclerosis); neurodegeneration associated with bacterial or viral infections, and diseases such as schizophrenia, anxiety, depression and acute/chronic pain, the use of these compounds for manufacture of corresponding medicaments, processes for the manufacture of these novel compounds and medicaments, containing them.

DETAILED DESCRIPTION OF THE INVENTION

This invention is directed to compounds of formula I above. The compounds of the invention are preferably by which is meant the substitutents at positions 3 and 4 are cis in relation to each other (e.g. both R$^1$ and X are S isomers, or both R$^1$ and X are R isomers).

In one embodiment of the compounds of this invention, X is —O—. An example of such a compound is 4-[2-(4-p-tolyloxy-piperidin-1-yl)-ethanesulfonyl]-phenol.

In another embodiment of the compounds of this invention, X is —CH$_2$—. An example of such a compound is 4[-2-(4-benzyl-piperidine-1-yl)-ethanesulfonyl]-phenol.

In compounds where X is —CH$_2$—, it is preferred that R$^1$ is hydroxy. In one embodiment, R$^2$ is hydrogen, especially where R$^1$ is hydroxy. Examples of such compounds are (+)(3R,4R)-4-benzyl-1-[2-(4-hydroxy-benzenesulfonyl)-ethyl]-piperidin-3-ol, (−)(3S,4S)-4-benzyl-1-[2-(4-hydroxy-benzenesulfonyl)-ethyl]-piperidin-3-ol, and (3RS,4RS)-4-benzyl-1-[2-(4-hydroxy-benzenesulfonyl)-ethyl]-piperidin-3-ol.

In other compounds where X is —CH$_2$—, it is preferred that R$^1$ is hydroxy. In one embodiment, R$^2$ is methyl, especially where R$^1$ is hydroxy. Examples of such compounds are, (+)(cis)-1-[2-(4-hydroxy-benzenesulfonyl)-ethyl]-4-(4-methyl-benzyl)-piperindin-3-ol,
(−)(cis)-1-[2-(4-hydroxy-benzenesulfonyl)-ethyl]-4-(4-methyl-benzyl)-piperidin-3-ol, and (3RS,4RS)-1-[2-(4-hydroxy-benzenesulfonyl)-ethyl]-4-(4-methyl-benzyl)-piperidin-3-ol.

The term "pharmaceutically acceptable acid addition salts" embraces salts with inorganic and organic acids, such as hydrochloric acid, nitric acid, sulfuric acid, lactic acid, phosphoric acid, citric acid, formic acid, fumaric acid, maleic acid, acetic acid, succinic acid, tartaric acid, methane-sulfonic acid, p-toluenesulfonic acid and the like.

The data in the following table demonstrates the high selectivity of compounds of the present invention.

4[-2-(4-benzyl-piperidine-1-yl)-ethanesulfonyl]-phenol (1),
4-[2-(4-p-tolyloxy-piperidin-1-yl)-ethanesulfonyl]-phenol (2),
(−)(3S,4S)-4-benzyl-1-[2-(4-hydroxy-benzenesulfonyl)-ethyl]-piperidin-3-ol (3),
(+)(3R,4R)-4-benzyl-1-[2-(4-hydroxy-benzenesulfonyl)-ethyl]-piperidin-3-ol (4),
(3RS,4RS)-4-benzyl-1-[2-(4-hydroxy-benzenesulfonyl)-ethyl]-piperidin-3-ol (5),
(−)(cis)-1-[2-(4-hydroxy-benzenesulfonyl)-ethyl]-4-(4-methyl-benzyl)-piperidin-3-ol (6),
(+)(cis)-1-[2-(4-hydroxy-benzenesulfonyl)-ethyl]-4-(4-methyl-benzyl)-piperidin-3-ol (7)
(3RS,4RS)-1[-2-(4-hydroxy-benzenesulfonyl)-ethyl]-4-(4-methyl-benzyl)-piperidin-3-ol (8)

Selectivity Profile of NMDA NR2B Subtype Selective Antagonists a) reacting a compound of formula

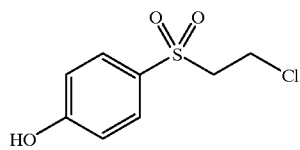

II with a compound of formula

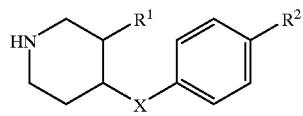

III to a compound of formula

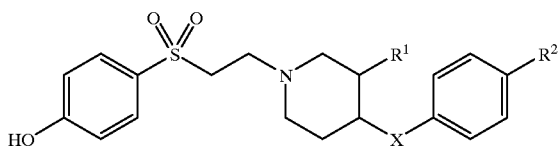

I wherein the substitutents are described above, and, if desired, b) converting the compound of formula I obtained into a pharmaceutically acceptable acid addition salts,
c) and, if desired,
converting a racemic mixture into its enantiomeric component thus obtaining optically pure compounds.

| Compound | Inhibition of 3H [R-(R*, S*)]-α-(4-Hydroxy-phenyl)-β-methyl-4-(phenyl-methyl)-1-piperidine propanol binding IC$_{50}$(μM)$^a$ | Inhibition of [3H]-Prazosin binding IC$_{50}$(μM)$^b$ | NMDA NR1 + NR2B IC$_{50}$ (μM)$^c$ | NMDA NR1 + NR2A IC$_{50}$ (μM)$^c$ | i.c.v. NMDA ED$_{50}$ mg/kg i.v.$^d$ | hERG IC$_{50}$(μM)$^e$ |
|---|---|---|---|---|---|---|
| (9) | 0.010 | 3.5 | 0.003 | >100 | 2.3 | 0.69 |
| (1) | 0.018 | 42 | <0.01 | >10 | 1.1 | 4.0 |
| (2) | 0.024 | 16 | <0.01 | >10 | 0.84 | 4.7 |
| (3) | 0.014 | 55 | 0.038 | >10 | 3.8 | >10 |
| (6) | 0.011 | 88 | 0.008 | >10 | 2.2 | 3.7 |

*(9)1-[2-(4-hydroxy-phenoxy)-ethyl]-4-(4-methyl-benzyl)-piperidin-4-ol comparison EP 824098
$^a$Inhibition of binding indicates affinity for NMDA NR2B subunit containing receptors.
$^b$Inhibition of binding indicates affinity for α$_1$-adrenergic receptors.
$^c$Indicates the ability to block selectively recombinant NMDA receptor subtypes expressed in Xenopus oocytes.
$^d$Indicates potency in mg/kg i.v. to block i.c.v. NMDA-induced convulsions in mice.
$^e$Indicates potency for blockade of recombinant human ERG potassium channels expressed in a mammalian cell line.

The novel compounds of formula I and their pharmaceutically acceptable salts can be prepared by methods known in the art, for example by processes described below, which comprises In accordance with process variant a) 4-(2-chloro-ethanesulfonyl)-phenol is dissolved in methylchloride and a compound of formula III, for example 4-p-tolyloxy-piperidine, 4-benzylpiperidine, (3S,4S)-4-benzyl-piperidine-3-ol, (cis)-4-(4-methyl-benzyl)-piperidine-3-ol is added and in the presence of triethylamine or an excess of the piperidine the solution is stirred for some hours at room temperature. The reaction mixture is purified by chromatography over silica gel.

The acid addition salts of the compounds of formula I are especially well suited for pharmaceutical use.

The following schemes 1–3 describe the preparation of compounds of formula I and of compounds of formulae XIII, XIV and VIII, which are intermediates. The starting materials of formulae V and XV are known compounds or can be prepared by methods known in the art.

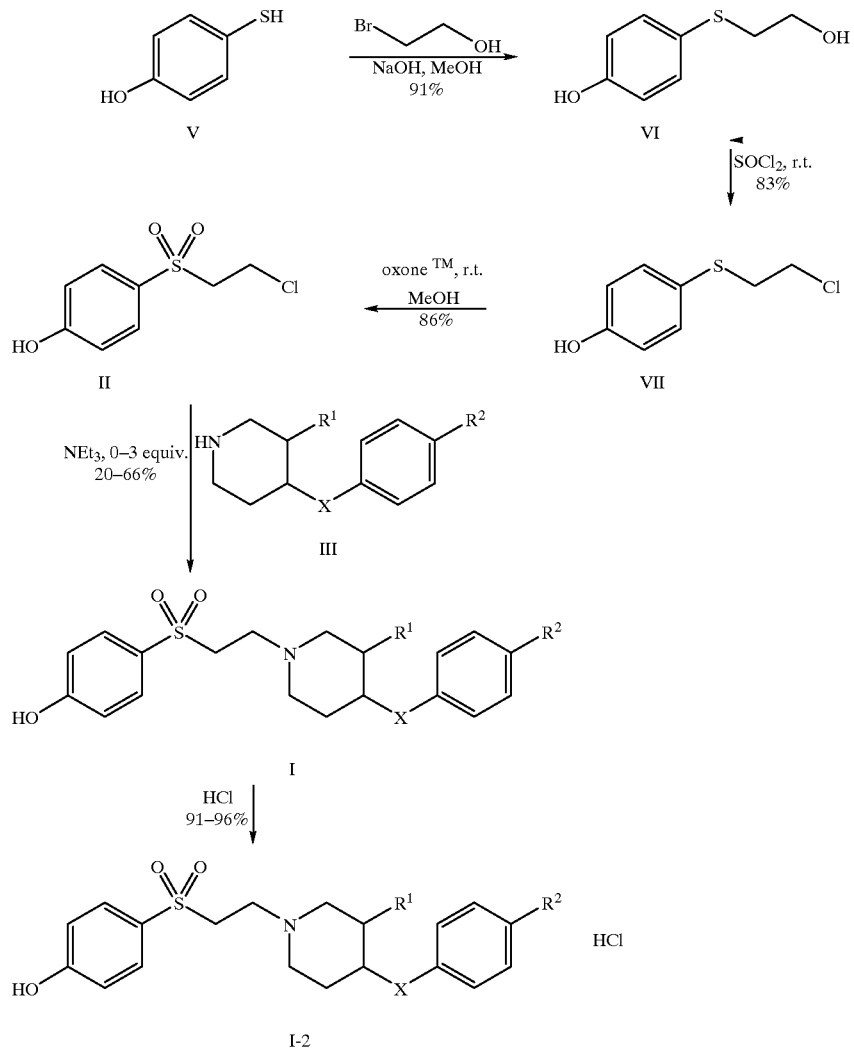

Scheme 2
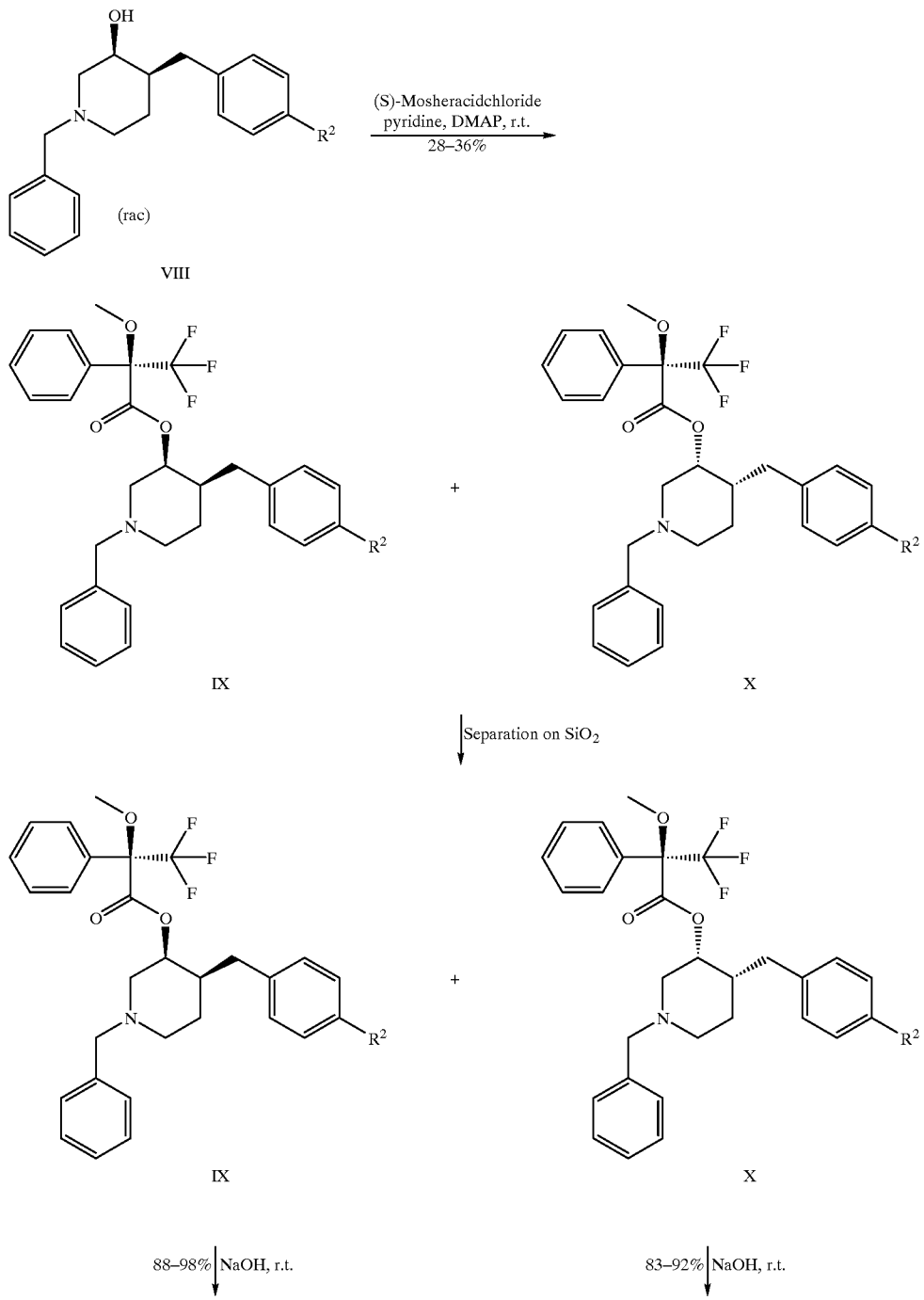

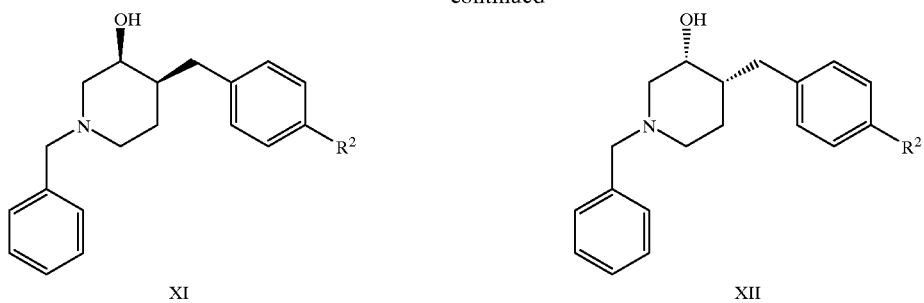
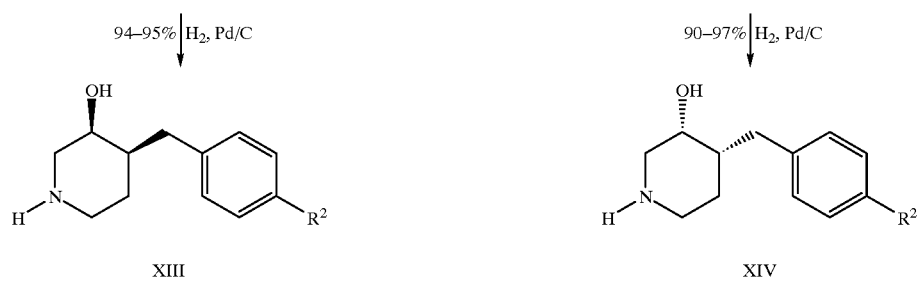
$R^2 = H, CH_3$
In Scheme 2 above it is shown the synthesis of enantiomerically pure 3-hydroxy benzylpiperidines.
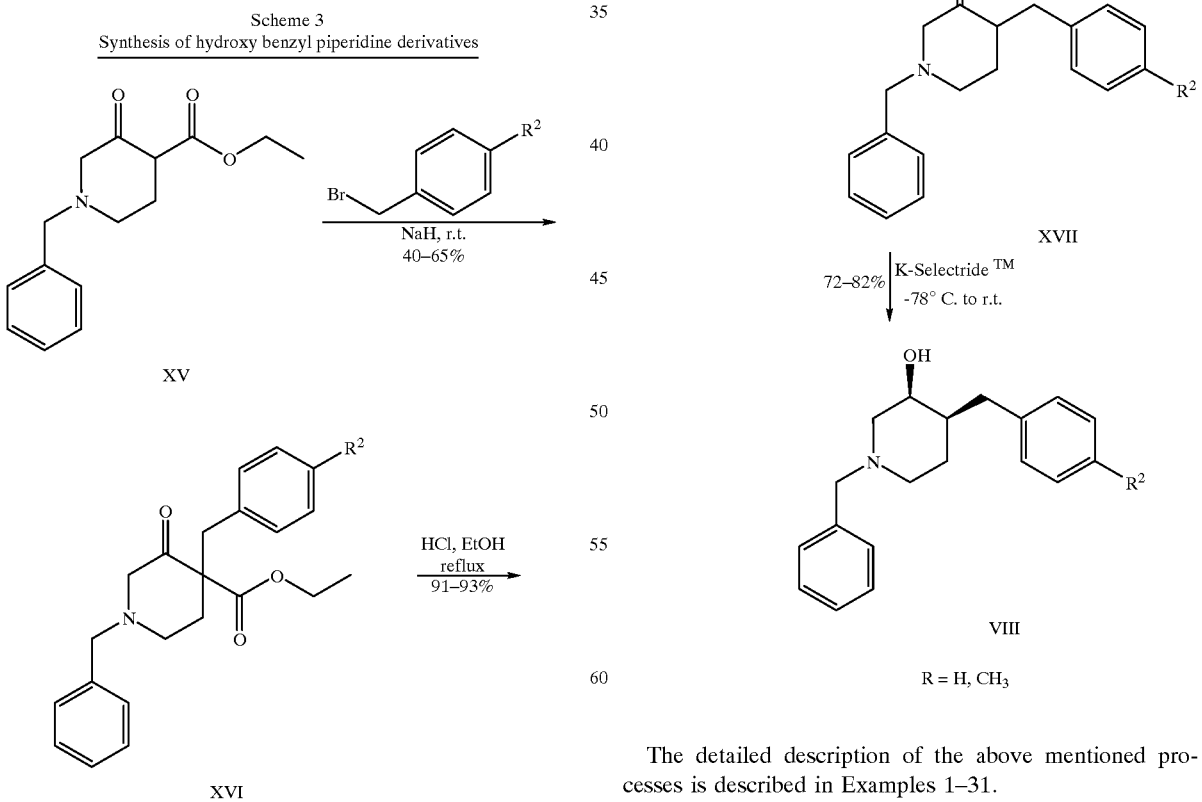
$R = H, CH_3$
The detailed description of the above mentioned processes is described in Examples 1–31.

As mentioned earlier, the compounds of formula I and their pharmaceutically acceptable addition salts possess valuable pharmacodynamic properties. They are NMDA-receptor subtype selective blockers, which have a key function in modulating neuronal activity and plasticity which makes them key players in mediating processes underlying development of CNS as well as learning and memory formation.

The compounds were investigated in accordance with the test given hereinafter.

Method 1

3H [R-(R*,S*)]-α-(4-Hydroxy-phenyl)-β-methyl-4-(phenyl-methyl)-1-piperidine propanol) binding Male Füllinsdorf albino rats weighing between 150–200 g were used. Membranes were prepared by homogenization of the whole brain minus cerebellum and medulla oblongata with a Polytron (10.000 rpm, 30 seconds), in 25 volumes of a cold Tris-HCl 50 mM, EDTA 10 mM, pH 7.1 buffer. The homogenate was centrifuged at 48.000 g for 10 minutes at 4° C. The pellet was resuspended using the Polytron in the same volume of buffer and the homogenate was incubated at 37° C. for 10 minutes. After centrifugation the pellet was homogenized in the same buffer and frozen at −100° C. for at least 16 hours but not more than 10 days. For the binding assay the homogenate was thawed at 37° C., centrifuged and the pellet was washed three times as above in a Tris-HCl 5 mM, pH 7.4 cold buffer. The final pellet was resuspended in the same buffer and used at a final concentration of 200 µg of protein/ml.

3H [R-(R*,S*)]-α-(4-Hydroxy-phenyl)-β-methyl-4-(phenyl-methyl)-1-piperidine propanol binding experiments were performed using a Tris-HCl 50 mM, pH 7.4 buffer. For displacement experiments 5 nM of 3H [R-(R*,S*)]-α-(4-Hydroxy-phenyl)-β-methyl-4-(phenyl-methyl)-1-piperidine propanol were used and non specific binding was measured using 10 µM of tetrahydroisoquinoline and usually it accounts for 10% of the total. The incubation time was 2 hours at 4° C. and the assay was stopped by filtration on Whatmann GF/B glass fiber filters (Unifilter-96, Packard, Zürich, Switzerland). The filters were washed 5 times with cold buffer. The radioactivity on the filter was counted on a Packard Top-count microplate scintillation counter after addition of 40 mL of microscint 40 (Canberra Packard S. A., Zürich, Switzerland).

The effects of compounds were measured using a minimum of 8 concentrations and repeated at least once. The pooled normalized values were analyzed using a non-linear regression calculation program which provide $IC_{50}$ with their relative upper and lower 95% confidence limits (RS1, BBN, USA).

Method 2

3H-Prazosin Binding

Male Füllinsdorf albino rats weighing between 150–200 g were used. Membranes were prepared by homogenization of the whole brain minus cerebellum and medulla oblongata with a Plytron (10.000 rpm, 30 seconds), in 25 volumes of a cold Tris-HCl 50 mM, EDTA 10 mM, pH 7.1 buffer. The homogenate was centrifuged at 48.000 g for 10 minutes at 4° C. The pellet was resuspended using the Polytron in the same volume of buffer and the homogenate was incubated at 37° C. for 10 minutes. After centrifugation the pellet was homogenized in the same buffer and frozen at −80° C. for at least 16 hours but not more than 10 days. For the binding assay the homogenate was thawed at 37° C., centrifuged and the pellet was washed three times as above in a Tris-HCl 15mM, pH 7.4 cold buffer. The final pellet was resuspended in the same buffer and used at a final concentration of 200 mg of protein/ml.

3H-Prazosin binding experiments were performed using a Tris-HCl 50 mM, pH 7.4 buffer. For displacement experiments 0.2 nM of 3H-Prazosine were used and non specific binding was measured using 100 mM of Chlorpromazine. The incubation time was 30 minutes at room temperature and the assay was stopped by filtration on Whatman GF/B glass fiber filters (Ubrifilter-96, Canberra Packard S. A., Zürich, Switzerland). The filters were washed 5 times with cold buffer. The radioactivity on the filter was counted on a Packard Top-count microplate scintillation counter after addition of 40 ml of microscint 40 (Canberra Packard S. A., Zürich, Switzerland). The effects of compounds were measured using a minimum of 8 concentrations and repeated at least once. The pooled normalized values were analyzed using a non-linear regression calculation program which provide $IC_{50}$ with their relative upper and lower 95% confidence limits (RS1, BBN, USA).

The thus-determined activity of compounds of examples 1–3 and 6 in accordance with the invention is in the range of 0.011–0.024 (in µM), as described in the table above.

Method 3

Methods for Studying the Inhibition of the HERG $K^+$ Channel

CHO cells were stably transfected by a pcDNA3-HERG expression vector containing a SV40-neo cassette for selection. Cells were thinly plated into 35 mm dishes and used for the electrophysiological experiment ½–3 d later.

During the experiment the cells were continuously super fused with an extracellular saline containing (in mM): NaCl 150, KCl 10, $MgCl_2$ 1, $CaCl_2$ 3, HEPES 10 (pH=7.3 by addition of NaOH). A 10-mM stock solution of the test compound was made from pure DMSO. Test solution were made by at least 1000-fold dilution of the stock solution into the extracellular saline. The glass micropipettes for whole-cell patch-clamp recording were filled with a containing (in mM): KCl 110, BAPTA 10, HEPES 10, $MgCl_2$ 4.5, $Na_2ATP$ 4, $Na_2$-phosphocreatine 20, creatine kinase 200 µg/ml (pH= 7.3 by addition of KOH).

The whole-cell configuration of the patch-clamp technique was used for the experiments. Cells were clamped to −80 mV holding potential and repetitively (0.1 Hz) stimulated by a voltage pulse pattern consisting of a 1-s conditioning depolarisation to 20 mV immediately followed by a hyperpolarisation of 50 ms duration to −120 mV. The membrane current was recorded for at least 3 min (18 stimuli) before compound application (control), and then for another two 3-min intervals in presence of two different concentrations of the compound. The current amplitudes ($I_{test}$) at the end of each compound application interval were divided by the mean current amplitude ($I_{control}$) during the initial control period to calculate the percentage effect of the compound:

$$\text{effect } (\%) = (1 - I_{test}/I_{control}) \cdot 100.$$

Compound concentrations were chosen in decade steps (usually 1 and 10 µM) around the expected 50% inhibitory concentration ($IC_{50}$). If after the first experiment the $IC_{50}$ turned out to lie outside the range between the two chosen concentrations the concentrations were changed to bracket the $IC_{50}$ in the following experiments. The compound was tested on at least three cells. Its $IC_{50}$ was then estimated from the population of all percent-effect values by non-linear regression using the function effect=100/(1−$IC_{50}$/concentration)$^{Hill}$).

Concentrations higher than 10 μM were not tested. If 10 μM of the compound turned out to produce less than 50% effect, IC50 was labelled as ">10 μM" and the compound was characterised by the average effect seen at 10 μM.

The compounds of formula I and their salts, as herein described, together with pharmaceutically inert excipients can be incorporated into standard pharmaceutical dosage forms, for example, for oral or parenteral application with the usual pharmaceutical adjuvant materials, for example, organic or inorganic inert carrier materials, such as, water, gelatin, lactose, starch, magnesium stearate, talc, vegetable oils, gums, polyalkylene-glycols and the like. Examples of pharmaceutical preparations in solid form are tablets, suppositories, capsules, or in liquid form are solutions, suspensions or emulsions. Pharmaceutical adjuvant materials include preservatives, stabilizers, wetting or emulsifying agents, salts to change the osmotic pressure or to act as buffers. The pharmaceutical preparations can also contain other therapeutically active substances. Therefore, this invention is also directed to a pharmaceutical composition comprising any compound of formula 1 and a pharmaceutically acceptable carrier, and optionally other components as provided above. A preferable composition includes a compound of formula I which is cis at positions 3 and 4. Other preferred compositions include a compound of example 1, 2, 3, 4, 5, 7, or 8, or a combination of these compounds. The amount of the compound is an amount effective to relieve neurodegeneration.

The daily dose of compounds of formula I to be administered varies with the particular compound employed, the chosen route of administration and the recipient. Representative of a method for administering the compounds of formula I is by the oral and parenteral type administration route. An oral formulation of a compound of formula I is preferably administered to an adult at a dose in the range of 1 mg to 1000 mg per day. A parenteral formulation of a compound of formula I is preferably administered to an adult at a dose in the range of from 5 to 500 mg per day. Therefore, this invention is also directed to a method for treating neurodegeneration by administering a pharmaceutical composition comprising any compound of formula 1 and a pharmaceutically acceptable carrier, and optionally other components as provided above. A preferable method requires a compound of formula I which is cis at positions 3 and 4. Other preferred methods require a compound of example 1, 2, 3, 4, 5, 7, or 8, or a combination of these compounds. The amount of the compound administered is an amount effective to relieve neurodegeneration, as described above.

The invention is further illustrated in the following examples.

EXAMPLE 1

4[-2-(4-Benzyl-piperidine-1-yl)-ethanesulfonyl]-phenol

To a solution of 40.0 g 4-(2-chloro-ethanesulfonyl)-phenol (181 mmol) in 600 ml $CH_2Cl_2$ were added 69.9 g 4-benzylpiperidine (399 mmol). After stirring for 16 h at r. t. the reaction mixture was concentrated to 100 ml and directly purified by chromatography over silica gel ($CH_2Cl_2$/MeOH/$NH_3$ 19/1/0.1). Recrystallization from ethyl acetatel-hexane (2:1) yielded 25 g product (70 mmol, 38%).

MS: m/e=360.2 (M+H$^+$).

4[-2-(4-Benzyl-piperidine-1-yl)-ethanesulfonyl]-phenol hydrochloride (1:1)

To a solution of 1.15 g 4[-2-(4-benzyl-piperidine-1-yl)-ethanesulfonyl]-phenol (3.2 mmol) in EtOH (5 ml) was added ethanolic HCl (2.6 ml, 1.46 M, 3.8 mmol). The reaction mixture was cooled to 0–5° C. and stirred for 10 min. Then diethyl ether was added until the product precipitated. After filtration 1.14 g of the product (2.9 mmol, 91%) as a white solid was obtained.

MS: m/e=360.2 (M+H$^+$).

Following the general procedure of example 1 the compounds of example 2 to example 8 were prepared.

EXAMPLE 2

4-[2-(4-p-Tolyloxy-piperidin-1-yl)-ethanesulfonyl]-phenol

The title compound was prepared from 4-(2-chloro-ethanesulfonyl)-phenol and 4-p-tolyloxy-piperidine (prepared according to J. Med. Chem., 1978, 21, 309) in 59% yield as a white solid.

MS: m/e=376.4 (M+H$^+$).

4-[2-(4-p-Tolyloxy-piperidin-1-yl)-ethanesulfonyl]-phenol hydrochloride (1:1)

The title compound was prepared from 4-[2-(4-p-tolyloxy-piperidin-1-yl)-ethanesulfonyl]-phenol in 96% yield as a white solid.

MS: m/e=376.4 (M+H$^+$).

EXAMPLE 3

(−)(3S,4S)-4-Benzyl-1-[2-(4-hydroxy-benzenesulfonyl)-ethyl]-piperidin-3-ol

The title compound was prepared from 4-(2-chloro-ethanesulfonyl)-phenol and (3S,4S)-4-benzyl-piperidine-3-ol in 66% yield as a white solid.

MS: m/e=376.4 (M+H$^+$), $[\alpha]_D^{20}$=−38.87 (c=1.11, chloroform).

EXAMPLE 4

(+)(3R,4R)-4-Benzyl-1-[2-(4-hydroxy-benzenesulfonyl)-ethyl]-piperidin-3-ol

The title compound was prepared from 4-(2-chloro-ethanesulfonyl)-phenol and (3R,4R)-4-benzyl-piperidine-3-ol in 50% yield as a white solid.

MS: m/e=376.4 (M+H$^+$), $[\alpha]_D^{20}$=+39.81 (c=1.66, chloroform).

EXAMPLE 5

(3SR,4SR)-4-Benzyl-1-[2-(4-hydroxy-benzenesulfonyl)-ethyl]-piperidin-3-ol

The title compound was from 4-(2-chloro-ethanesulfonyl)-phenol and (3SR,4SR)-4-benzyl-piperidine-3-ol in 20% yield as a white foam.

MS: m/e=376.4 (M+H$^+$).

EXAMPLE 6

(−)(cis)-[1-2-(4-Hydroxy-benzenesulfonyl)-ethyl]-4-(4-methyl-benzyl)-piperidin-3-ol The compound was prepared from 4-(2-chloro-ethanesulfonyl)-phenol and (3R,4R)- or (3S,4S)-4-(4-methyl-benzyl)-piperidin-3-ol in 51% yield as a white foam.

MS: m/e=390.2 (M+H$^+$), $[\alpha]_D^{20}$=−38.27 (c=1.02, chloroform).

EXAMPLE 7

(+)(cis)1-[2-(4-Hydroxy-benzenesulfonyl)-ethyl]-4-(4-methyl-benzyl)-piperidin-3-ol The title compound was prepared from 4-(2-chloroethanesulfonyl)-phenol and (3R,4R)-4-(4-methyl-benzyl)-piperidin-3-ol in 31% yield as a white foam.

MS: m/e=390.3 (M+H$^+$), $[\alpha]_D^{20}$=+39.01 (c=1.05, chloroform).

EXAMPLE 8

(3SR,4SR)-1-[2-(4-Hydroxy-benzenesulfonyl)-ethyl]-4-(4-methyl-benzyl)-piperidin-3-ol The title compound was prepared from 4-(2-chloroethanesulfonyl)-phenol and (3SR,4SR)-4-(4-methyl-benzyl)-piperidin-3-ol in 30% yield as a white solid.

MS: m/e=390.3 (M+H$^+$).

Preparation of Intermediates

EXAMPLE 9

(3R,4R)-4-Benzyl-piperidine-3-ol (3R,4R)-1,4-Dibenzyl-piperidine-3-ol (320 mg, 1.1 mmol) was dissolved in 10 ml ethanol and hydrogenated in the presence of Pd on C (10%, 70 mg) under atmospheric pressure at 50° C. for 2 h. The reaction mixture was filtrated and washed with ethanol to give 205 mg of the product (1.1 mmol, 94%) as a white solid.

MS: m/e=191 (M+H$^+$), $[\alpha]_D^{20}$=+42.8 (c=1.17, chloroform).

Following the general procedure of example 9 the compounds of example 10 to example 14 were prepared

EXAMPLE 10

(3S,4S)-4-Benzyl-piperidine-3-ol

The title compound was prepared from (3S,4S)-1,4-dibenzyl-piperidine-3-ol in 97% yield as a colorless oil.

MS: m/e=191 (M), $[\alpha]_D^{20}$=−41.1 (c=1.14, chloroform).

EXAMPLE 11

(3SR,4SR)-4-Benzyl-piperidine-3-ol

The title compound was repared from (3SR,4SR)-1,4-dibenzyl-piperidine-3-ol in 88% yield as a colorless oil.

MS: m/e=191 (M).

EXAMPLE 12

(cis)-4-(4-Methyl-benzyl)-piperidin-3-ol

The title compound was prepared from(3R, 4R)-1-benzyl-4-(4-methyl-benzyl)-piperidin-3-ol in 95% yield as a colorless oil.

MS: m/e=206.2 (M+H$^+$), $[\alpha]_D^{20}$+40.2 (c=0.90, chloroform).

EXAMPLE 13

(cis)-4-(4-Methyl-benzyl)-piperidin-3-ol

The title compound was prepared from (cis)-1-benzyl-4-(4-methyl-benzyl)-piperidin-3-ol in 90% yield as a colorless oil.

MS: m/e=206.2 (M+H$^+$), $[\alpha]_D^{20}$=−38.1 (c=0.93, chloroform).

EXAMPLE 14

(3SR,4SR)-4-(4-Methyl-benzyl)-piperidin-3-ol

The title compound was prepared from (3SR,4SR)-1-benzyl-4-(4-methyl-benzyl)-piperidin-3-ol in quantitative yield as a colorless oil.

MS: m/e=206.2 (M+H$^+$).

EXAMPLE 15

(3R,4R)-1,4-Dibenzyl-piperidine-3-ol

To a solution of 700 mg (R)-3,3,3-trifluoro-2-methoxy-2-phenyl-propionic acid (3R, 4R)-1,4-dibenzyl-piperidin-3-yl ester (1.4 mmol) in 15 ml ethanol were added at r.t. 7 ml 4N NaOH (28 mmol). After 16 h the reaction mixture was poured to a 1:1 mixture of water and CH$_2$Cl$_2$ and the organic layer was separated. The aqueous phase was extracted twice with CH$_2$Cl$_2$ and the combined organic layers were washed with water, dried over MgSO$_4$ and the solvent was removed under reduced pressure to give 350 mg of the product (12.4 mmol, 88%) as a yellow solid.

MS: m/e=281 (M), $[\alpha]_D^{20}$=+45.1 (c=1.11, chloroform).

Following the general procedure of example 15 the compounds of example 16 to example 18 were prepared.

EXAMPLE 16

(3S,4S)-1,4-Dibenzyl-piperidine-3-ol

The title compound was prepared from (R)-3,3,3-trifluoro-2-methoxy-2-phenyl-propionic acid (3S,4S)-1,4-dibenzyl-piperidin-3-yl ester in 83% yield as a yellow solid.

MS: m/e=281 (M), $[\alpha]_D^{20}$=−44.8 (c=1.13, chloroform).

EXAMPLE 17

(cis)-1-Benzyl-4-(4-methyl-benzyl)-piperidin-3-ol

The title compound was prepared from (R)-3,3,3-trifluoro-2-methoxy-2-phenyl-propionic acid (cis)-1-benzyl-4-(4-methyl-benzyl)-piperidin-3-yl ester in 98% yield as a yellow oil.

MS: m/e=296.4 (M+H$^+$), $[\alpha]_D^{20}$=+40.7 (c=1.13, chloroform).

EXAMPLE 18

(cis)-1-Benzyl-4-(4-methyl-benzyl)-piperidin-3-ol

The title compound was prepared from (R)-3,3,3-trifluoro-2-methoxy-2-phenyl-propionic acid (cis)-1-benzyl-4-(4-methyl-benzyl)-piperidin-3-yl ester in 92% yield as a colorless oil.

MS: m/e=296.4 (M+H$^+$), $[\alpha]_D^{20}$=−42.8 (c=1.13, chloroform).

EXAMPLE 19

(R)-3,3,3-Trifluoro-2-methoxy-2-phenyl-propionic (3R,4R)-1,4-dibenzyl-piperidin-3-yl ester To a solution of 1.50 g (3SR,4SR)-1,4-dibenzyl-piperidine-3-ol (53 mmol) in 50 ml CH$_2$Cl$_2$were added at 0° C. 0.515 ml pyridine (506 mg, 64 mmol), 912 mg dimethylaminopyridine (74.6 mmol) and 1.19 ml (S)-(+)-alphamethoxy-alpha-trifluoromethylphenylacetyl chloride (1.62 g, 64 mmol). The reaction mixture was stirred for 5 h at r.t., quenched by the addition of 50 ml water and stirred for 30 min. The organic phase was separated and washed twice with 50 ml saturated NaHCO$_3$-solution. The combined aqueous phases were extracted with CH$_2$Cl$_2$ and the combined organic phases were dried over MgSO$_4$. The solvent was removed under reduced pressure and the crude product was purified by chromatography over silica gel (CH$_2$Cl$_2$/hexane/NH$_3$ 50/50/1) to give 750 mg of the product (15.1 mmol, 28%) as a yellow oil.

MS: m/e=498.2 (M+H$^+$), $[\alpha]_D^{20}$=+106.0 (c=1.02, chloroform).

Following the general procedure of example 19 the compounds of example 20 to example 22 were prepared.

EXAMPLE 20

(R)-3,3,3-trifluoro-2-methoxy-2-phenyl-propionic acid (3S,4S)-1,4-dibenzyl-piperidin-3-yl ester The title compound was prepared from (3SR,4SR)-1,4-dibenzyl-piperidin-3-ol and (S)-(+)-alpha-methoxy-alpha-trifluoromethylphenylacetyl chloride in 29% yield as a yellow oil.

MS: m/e=498.3 (M+H$^+$), $[\alpha]_D^{20}$=−65.8 (c=0.89, chloroform).

EXAMPLE 21

(R)-3,3,3-trifluoro-2-methoxy-2-phenyl-propionic acid (cis)-1-benzyl-4-(4-methyl-benzyl)-piperidin-3-yl ester The title compound was prepared from (3SR,4SR)-4-(4-methyl-benzyl)-piperidin-3-ol and (S)-(+)-alpha-methoxy-alpha-trifluoromethylphenylacetyl chloride in 33% yield as a yellow oil.

MS: m/e=512.3 (M+H$^+$), $[\alpha]_D^{20}$=+102.0 (c=0.98, chloroform).

EXAMPLE 22

(R)-3,3,3-trifluoro-2-methoxy-2-phenyl-propionic acid (cis)-1-benzyl-4-(4-methyl-benzyl)-piperidin-3-yl ester The title compound was prepared from (3SR,4SR)-4-(4-methyl-benzyl)-piperidine-3-ol and (S)-(+)-alpha-methoxy-alpha-trifluoromethylphenylacetyl chloride in 36% yield as a yellow oil.

MS: m/e=512.4 (M+H$^+$), $[\alpha]_D^{20}$=−63.1 (c=1.06, chloroform).

EXAMPLE 23

(3SR,4SR)-1,4-Dibenzyl-piperidin-3-ol

To a solution of 9.0 g (SR)-1,4-dibenzyl-piperidin-3-one (32 mmol) in 200 ml dry THF were added at −78° C. dropwise 48 ml K-selectride® (1 N in THF, 48 mmol). The reaction mixture was stirred for 1 h at −70° C. and then warmed to r.t. The reaction was quenched by the addition of 100 ml NaHCO$_3$-solution and the aqueous phase was extracted twice with ethyl acetate (200 ml). The combined organic phases were washed with water (100 ml) and brine (100 ml). The organic phase was dried over MgSO$_4$, filtrated and the solvent was removed under reduced pressure to give the crude product. Purification by chromatography (ethyl acetate/hexane 1/2 to 2/1) yielded 6.5 g of the product (23 mmol, 72%) as a yellow oil.

MS: m/e=281 (M).

Following the general procedure of example 23 the compound of example 24 was prepared.

EXAMPLE 24

(3SR,4SR)-1-Benzyl-4-(4-methyl-benzyl)-piperidin-3-ol

The title compound was prepared from (SR)-1-benzyl-4-(4-methyl-benzyl)-piperidin-3-one in 82% yield as an orange oil.

MS: m/e=296.4 (M+H$^+$).

EXAMPLE 25

(RS)-1,4-Dibenzyl-piperidin-3-one

To a solution of 13.5 g (SR)-1,4-dibenzyl-3-oxo-piperidine-4-carboxylic acid ethyl ester (38.4 mmol) in 20 ml ethanol were added 47.5 ml HCl (37%) and the yellow solution was refluxed for 48 h. The reaction mixture was cooled to 0° C. and NaOH was added until pH 8 was reached. The aqueous phase was extracted three times with ethyl acetate (200 ml) and the combined organic phases were washed with water (2×100 ml) and brine (2×100 ml). The organic phase was dried over MgSO$_4$, filtrated and the solvent was removed under reduced pressure to give 9.8 g of the product (35 mmol, 91%) as a brown oil.

MS: m/e=279 (M).

Following the general procedure for example 25 the compound of example 26 was prepared.

EXAMPLE 26

(SR)-1-Benzyl-4-(4-methyl-benzyl)-piperidin-3-one

The title compound was prepared from (SR)-1-benzyl-4-(4-methyl-benzyl)-3-oxo-piperidine-4-carboxylic acid ethyl ester in 77% yield as a brown oil.

MS: m/e=294 (M+H$^+$).

EXAMPLE 27

(SR)-1,4-Dibenzyl-3-oxo-piperidine-4-carboxylic acid ethyl ester

To a suspension of 30.9 g NaH (55%, 772 mmol) in 1000 ml DMF was added under argon atmosphere portionwise 115 g ethyl (SR)-N-benzyl-3-oxo-4-piperidine-carboxylate hydrochloride (386 mmol, commercially available) at 0–5° C. The reaction mixture was stirred for 1 h at r.t. and a solution of 45.9 ml benzylbromide (66.0 g, 386 mmol) in 200 ml DMF was added at 0° C. The reaction mixture was stirred for 1.5 h at r. t. and 200 ml sat. NaHCO$_3$ solution were added at 0–10° C. The reaction mixture was reduced to 500 ml and 1000 ml water were added. The aqueous phase was extracted three times with 1000 ml ethyl acetate and the combined organic phases were washed with water (3×200 ml) and brine (3×200 ml). The organic phase was dried over MgSO$_4$, filtrated and the solvent was removed under reduced pressure. The crude product was purified by chromatography over silica gel (ethyl acetate/hexane 1/8, then 1/4) to give 101 g of the product (290 mmol, 75%) as a brown oil.

MS: m/e=352.4 (M+H⁺).

Following the general procedure for example 27 the compound of example 28 was prepared.

EXAMPLE 28

(SR)-1-Benzyl-4-(4-methyl-benzyl)-3-oxo-piperidine-4-carboxylic acid ethyl ester The title compound was prepared from (SR)-N-benzyl-3-oxo-4-piperidine-carboxylate hydrochloride and 4-methyl-benzylbromide in 73% yield as a brown oil.

MS: m/e=366.4 (M+H⁺).

EXAMPLE 29

4-(2-Chloro-ethanesulfonyl)-phenol

To a solution of 4.6 g 4-(2-chloro-ethylsulfanyl)-phenol (24.4 mmol) in 100 ml MeOH were added at r.t. 22.5 g oxone® (36.6 mmol). The reaction mixture was stirred for 16 h at r.t., filtrated and the solid was washed with MeOH. The filtrate was concentrated under reduced pressure, dissolved in ethyl acetate and washed twice with water. The combined aqueous phases were extracted twice with ethyl acetate. The combined organic layers were dried over MgSO₄ and the solvent was removed under reduced pressure. The crude product was purified by chromatography over silica gel (ethyl acetate/hexane 1/3) to give 4.6 g of the product (20.9, 86%) as a white solid.

MS: m/e=220 (M).

EXAMPLE 30

4-(2-Chloro-ethylsulfanyl)-phenol

To a solution of 5.0 g 4-(2-hydroxy-ethylsulfanyl)-phenol (29 mmol) in 100 ml CH₂Cl₂ were added at 0° C. 2.6 ml pyridine (32.3 mmol) and 2.34 ml SOCl₂ (32.3 mmol), dissolved in 10 ml CH₂Cl₂. The reaction mixture was stirred for 1 h at r.t. and then quenched by the addition of water. The organic phase was separated and washed twice with sat. NaHCO₃-solution. The combined aqueous phases were extracted with CH₂Cl₂ twice and the combined organic layers were dried over MgSO₄ and the solvent was removed under reduced pressure to give 4.6 g product (24.3 mmol, 83%) as a yellow oil.

MS: m/e=188 (M).

Example 31

4-(2-Hydroxy-ethylsulfanyl)-phenol

To a solution of 10.9 g 4-hydroxythiophenol (87 mmol) in 200 ml MeOH was added at 0–5° C. 87 ml 1N NaOH (87 mmol). After the reaction mixture was stirred for 10 min 6.1 ml bromoethanol (86 mmol) dissolved in 100 ml MeOH was added. The reaction mixture was stirred for 3 h at r.t. and the methanol was partly removed under reduced pressure. The residue was poured to a 1:1 mixture of ethyl acetate and saturated NaHCO₃-solution and the organic phase was separated, dried over MgSO₄, filtrated and the solvent was removed under reduced pressure. The residue was purified by chromatography over silica gel (ethyl acetate/hexane 3/2 to 2/1) to give 13.4 g product (78.7 mmol, 91%) as a white solid.

MS: m/e=170 (M).

Compounds of this invention are also made in accordance with Examples A–J as follows:

Example A

Preparation of 4-(benzyl-ethoxycarbonylmethyl-amino)-butyric acid ethyl ester

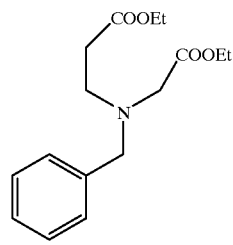

Example A.1.

A solution of 4.9 ml (25.8 mmol) N-benzylglycine ethyl ester and 7.7 ml (51.7 mmol) ethyl-4-bromobutyrate in 40 ml dimethylformamide (DMF) was treated at room temperature with 9.0 ml (64.3 mmol) triethylamine. The reaction mixture was heated to 65° C. and stirred for 23 h, subsequently cooled to room temperature and DMF was evaporated. The residue was treated with 100 ml water and 100 ml ethyl acetate. The phases were separated after extraction, the organic phase washed twice with total 100 ml water and the combined organic phase dried over Na₂SO₄. The solvent was removed under reduced pressure and the residue purified by chromatography over silica gel (hexane: ethyl acetate=9:1) to yield 7.1 g (88.8%) product as yellow oil.

MS (ISP): 308 (100, [M+H]⁺)

Example A.2.

To a solution of 2.57l (17.25 mol) ethyl-4-bromobutyrate in 10 l dioxane was added at 100° C. 1.72 kg (8.54 mol) N-benzylglycine ethyl ester. The reaction mixture was treated under reflux dropwise over a period of 6 h with 3.10 l (22.24 mol) triethylamine and subsequently stirred under reflux for 16 h. The suspension was cooled to 50° C. and treated with 10 l toluene, stirred at 0° C. for 1 h and afterwards filtered. The filtrate was concentrated to yield 3.08 kg crude product.

Example B.

Preparation of ethyl N-benzyl-3-oxo-4-piperidinecarboxylate hydrochloride

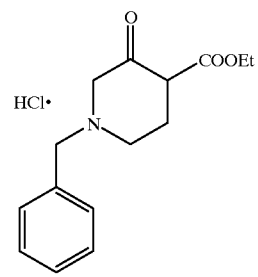

Example B.1.

A solution of 2.8 g (9.1 mmol) 4-(benzyl-ethoxycarbonylmethyl-amino)-butyric acid ethyl ester in 18 ml toluene was treated at room temperature with 980.0 mg (13.7 mmol) sodium ethoxide. The reaction mixture was heated to 85° C. and stirred for 3.5 h. After cooling to room temperature the reaction mixture was poured onto 50 ml ice-water, treated with 50 ml toluene and subsequently extracted. The aqueous phase was extracted with total 100 ml ethyl acetate, the organic phase washed twice with total 100 ml water and the combined organic phase dried over $Na_2SO_4$. The solvent was removed under reduced pressure to yield 2.2 g crude product. This crude product was treated with 3.7 ml of a solution of HCl in methyl alcohol 20%-weight and subsequently the solvent was removed under reduced pressure to yield 2.4 g crude product as white crystals. The crystals were dissolved under reflux in 30 ml isopropanol and the solution cooled to room temperature and stirred at this temperature for 2 h. The formed crystals were separated on a filter funnel and washed with 3 ml isopropanol (4° C.) and dried to yield 1.8 g (67.5%) product as white crystals.

MS (ISP): 262 (100, [M+H]$^+$).

Example B.2.

A solution of 2.02 kg (5.60 mol) crude 4-(benzyl-ethoxycarbonylmethyl-amino)-butyric acid ethyl ester from Example 1.2. in 10 l toluene was treated at room temperature with 0.79 kg (11.03 mol) sodium ethoxide (exothermic). The reaction mixture was heated to 85° C. and stirred for 3.5 h. The so formed suspension was cooled to room temperature and treated with 5 l toluene and 0.5 kg dicalite speedex. After neutralization by slowly addition of 0.71 acetic acid the suspension was filtered. The filtrate was concentrated to a volume of 9 l and treated with 1.4 l (6.86 mol) HCl in ethanol (4.9 M). After formation of crystals the ethanol was exchanged under reduced pressure by addition of 8 l toluene. The so formed suspension was treated with 5 l toluene, stirred at 0° C. for 16 h and subsequently filtered. The crystals were dried to yield 1.62 kg (94%) product.

Example C

Preparation of 1,4-dibenzyl-3-oxo-piperidine-4-carboxylic acid ethyl ester

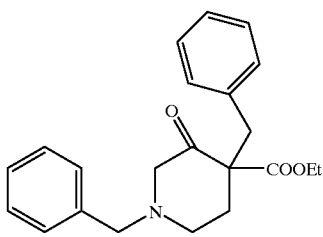

Example C.1

A mixture of 38.3 g (341.0 mmol) potassium tert.-butoxide and 625 ml absolute tetrahydrofuran was stirred at room temperature for 0.5 h. The resulting milky solution was cooled to 0° C. and then 50.0 g (168.0 mmol) ethyl N-benzyl-3-oxo-4-piperidine carboxylate hydrochloride were added via a powder dropping funnel. The temperature was kept below 5° C. The mixture was warmed up to room temperature and further stirred for 1 h resulting in a yellow solution. After cooling to 0° C., a solution of 30.2 g (176.0 mmol) benzyl bromide in 20.0 ml of absolute tetrahydrofuran was dropwise added in 0.5 h. A maximum temperature of 2° C. was observed. The reaction mixture was warmed to room temperature and stirred for 4 h. The reaction solution was cooled to 0° C. and 200 ml saturated ammonium chloride solution was slowly added. After extraction and phase separation, the aqueous phase was extracted twice with 100 ml of ethyl acetate. The combined organic phase were washed twice with 100 ml of saturated sodium chloride solution, dried over $Na_2SO_4$, the solvent evaporated under reduced pressure and the residue dried to yield 58.3 g (99.3%) crude product.

MS (ISP): 352 (100, [M+H]$^+$), 174 (15).

Example D

Preparation of rac-1,4-dibenzyl-3-oxo-piperidine hydrochloride

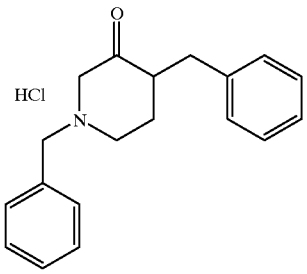

A solution of 118.0 g (336 mmol) crude rac-1,4-dibenzyl-3-oxo-piperidine-4-carboxylic acid ethyl ester in 118.0 ml of absolute ethanol was cooled to 0° C. and subsequent 405 ml (4.9 mol) 37% hydrochloric acid was cautiously added. The reaction temperature was kept below 7° C. Finally the mixture was heated under reflux for 19 h. To the dark brown solution were added some crystals of rac-1,4-dibenzyl-3-oxo-piperidine hydrochloride, then the mixture was allowed to cooled to room temperature and further stirred for 2 h. The resulting crystals, after recuperation on a Buchner funnel and washing twice with 60 ml of deionized water, were dried to yield 102.2 g crude product. Then 400 ml of ethyl acetate was added to the crude product and the mixture refluxed for 2 h and cooled afterwards to room temperature. The resulting beige suspension was filtered, the crystals were washed twice with 50 ml of ethyl acetate and dried to yield 82.2 g (78% over two steps) product.

MS (ISP): 280 (100, [M+H]$^+$), 262 (9).

M.p. 202–203° C.

Example E

Preparation of cis-1,4dibenzyl-3-hydroxy-piperidine

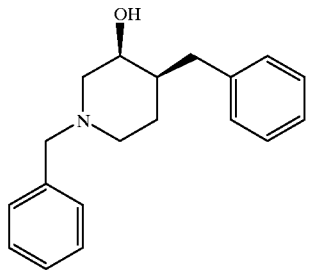

or

-continued

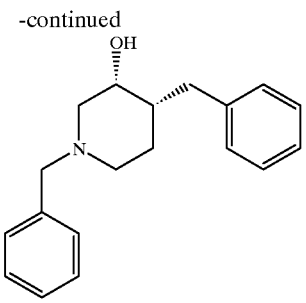

Example E.1
(S/C 50,000)

In the glove box (O2 content <=2 ppm) a 20 ml measuring flask was charged with 14.03 mg of [RuCl$_2$((S)-3,5-Xyl-MeOBIPHEP)((R,R)-DPEN)] (0.050 mmol) and filled to the graduation mark with 20 ml of isopropanol. The clear yellow catalyst solution was stirred with a magnetic stirring bar for 20 min at room temperature. The Ru-complex had been prepared by reaction of (S)-3,5-Xyl-MeOBIPHEP, [RuCl$_2$(COD)]$_n$ and (R,R)-DPEN in analogy to Angew. Chem. Int. Ed. 1998, 37, 1703–1707. In the glove box a glass flask was charged with 41.06 g (0.130 mol) of 1,4-dibenzyl-piperidin-3-one hydrochloride, 205 ml of isopropanol and 17.51 g (0.156 mol) of potassium tert.-butylate. The resulting suspension was stirred for 10 min and transferred into a 380 ml stirred stainless steel autoclave followed by 4.0 ml of catalyst solution (S/C 50,000). The autoclave was then sealed and connected to a hydrogenation line. The hydrogenation was carried out while stirring at room temperature at a total pressure of $4 \times 10^6$ Pa. After 3 h the hydrogenation mixture (a yellow suspension) was removed from the autoclave. A sample thereof was filtered, evaporated to dryness and analyzed as follows:

a) A 25-mg sample was dissolved in 0.8 ml of pyridine and silylated with 0.2 ml of commercial N,O-bis-(trimethylsilyl)-acetamide (BSA)+5% trimethylchlorosilane (TMS)-solution. Gas chromatographic analysis on a Permaphase PVMS/54 column showed complete conversion and a cis/trans ratio of 99:1. Retention times: 10.65 min (trans-1,4-dibenzyl-piperidin-3-ol), 10.80 min (cis-1,4-dibenzyl-piperidin-3-ol), 11.15 min (rac-1,4-dibenzyl-piperidin-3-one).
  b) ca. 0.6 ml sample of reaction mixture was taken up in water/ethyl acetate mixture and treated with a 5% ammonium chloride solution. The organic phase was dried (Na$_2$SO$_4$). HPLC analysis of an aliquot containing ca. 5–10 mg of product confirmed that the cis/trans-ratio was 99:1 and showed the enantiomeric purity (ee) of (S,S)- cis-1,4-dibenzyl-piperidin-3-ol to be 91%. Column: 2x Chiralpak AS, (250×4.6 mm), Daicel Chemicals Industries, Cat. No. 20025; Mobile phase: 1% (v/v) ethanol in n-hexane; flow 1.2 ml/min; pressure $6 \times 10^5$ Pa. The following retention times were observed: 11.2 min cis-(R,R)-product; 12.5 min cis-(S,S)-product; 17.5 and 19.5 min starting material (two enantiomers), 17.5 and 19.5 min trans-product (two enantiomers).

(3,5-Xyl)-MeOBIPHEP is (6,6'-Dimethoxybiphenyl-2,2'-diyl)bis[bis(3,5-dimethylphenyl]phosphine); DPEN is (1,2-Diphenylethylenediamine) (COD is 1,5-cyclooctadiene).

Example E.2
(S/C=100,000)

In a manner analogous to Example E.1, 41.06 g of rac-1,4-dibenzyl-piperidin-3-one hydrochloride was asymmetrically hydrogenated in the presence of 7 mg of [RuCl$_2$((S)-3,5-iPr-MeOBIPHEP)((R,R)-DPEN)] for 16 hours to afford after work-up (S,S)- cis-1,4-dibenzyl-piperidin-3-ol of 97% ee. ((3,5-iPr)-MeOBIPHEP is 6,6'-Dimethoxybiphenyl-2,2'-diyl)bis[bis(3,5-diisopropylphenyl)phosphine).

Example F

Preparation of (3S,4S)-4-benzyl-piperidine-3-ol (work-up after hydrogenation and deprotection of the amino group)

Example F.1

The reaction mixture from Example E.1 was treated with 300 ml ethyl acetate, 170 ml water, 50 ml 5% aqueous NH$_4$Cl solution and solid NaCl to saturate the aqueous phase. After phase separation, the aqueous phase was extracted twice with 200 ml ethyl acetate and the organic phases were washed twice with 150 ml brine. The combined organic phase was dried over Na$_2$SO$_4$, the solvent evaporated under reduced pressure to yield 35.6 g crude material as light-yellow crystals. This material was dissolved in 400 ml ethanol, treated at room temperature with 6.7 g (6.3 mmol) Pd/C 10% and stirred under H$_2$ at 55° C. for 2 h. Subsequent filtration and evaporation of the solvent yielded 25.3 g crude product as amorphous material. This crude product was dissolved at 100° C. in 100 ml toluene, cooled to 65° C. and treated with 125 ml hexane. The so formed suspension was cooled to 35° C. and treated again with 125 ml hexane. The suspension was stirred for 48 h at 0° C. and filtered afterwards to yield 10.0 g (ee=99.8%) product as white crystals. The mother liquor (13.9 g) was dissolved at 90° C. in 45 ml toluene treated at 55° C. with 55 ml hexane, cooled to 45° C. and added again 55 ml hexane. The suspension was stirred 16 h at room temperature and 3 h at 0° C., filtered to yield 9.7 g (ee=99.9%) product as white crystals. (Overall yield 81.5%)

MS (EI): 191 (100, [M]), 118 (76), 91 (44), 30 (100).

M.p. 91.5–92.5° C.

Example F.2
(work-up after hydrogenation, deprotection of the amino group and crystallization in presence of a resolving agent)

The reaction mixture from Example E.1 was treated with 10 ml 5% aqueous NH$_4$Cl solution and concentrated under reduced pressure to a total volume of 50 ml. This residue was treated with 50 ml water, 16 g NaCl, 50 ml 5% aqueous NH$_4$Cl solution and extracted twice with 100 ml ethyl acetate. The organic phases were washed twice with 100 ml brine, the combined organic phase was dried over Na$_2$SO$_4$ and the solvent evaporated under reduced pressure. The residue was dissolved in 105 ml ethanol, treated at room temperature with 1.8 g (1.7 mmol) Pd/C 10% and stirred under H$_2$ at 55° C. for 2.5 h. Subsequent filtration and evaporation of the solvent yielded 6.2 g crude product as yellow oil. The crude product was dissolved in 180 ml methanol and treated at 65° C. with a solution of 6.2 g (15.73 mmol) of (+)-di-O,O'-p-tolyl-D-tartaric acid in 25 ml methanol. The suspension was cooled to room temperature, stirred 48 h at this temperature, cooled to 0° C. and stirred for 2 h. The suspension was filtered to yield 9.2 g (ee=98.9%) salt as white crystals. 9.09 g of this product was dissolved in 460 ml methanol, stirred 1 h under reflux, cooled slowly to room temperature and stirred for 16 h at room temperature The suspension was cooled to 0° C., treated with 460 ml diethyl ether and stirred for 3 h. The suspension was filtered to yield 8.65 g (72.5%) salt. 4.02 g of this salt was dissolved in 40 ml CH$_2$Cl$_2$ and treated with 20 ml aqueous NaOH 1N. After extraction and phase separation, the aqueous phase was extracted twice with 20 ml CH$_2$Cl$_2$ and the combined organic phase dried over Na$_2$SO$_4$. The solvent was removed under reduced pressure to yield 2.0 g (100%, ee=99.6%) product. Overall yield was 72.5%.

Example G

Preparation of (3S,4S)-4-benzyl-1-[2-(4-hydroxy-benzenesulfonyl)-ethyl]-piperidin-3-ol

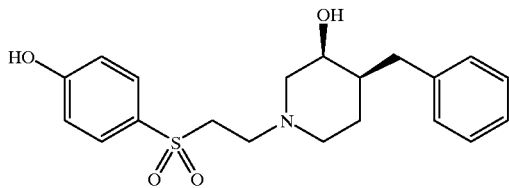

Example G.1

A solution of 5.5 g (24.4 mmol) 4-(2-chloro-ethane-sulfonyl)-phenol in 50 ml CH$_2$Cl$_2$ was treated at 37° C. with 3.7 ml (26.4 mmol) triethylamine and stirred for 3.25 h. Afterwards a solution of 4.5 g (22.0 mmol) (3S,4S)-4-benzyl-piperidin-3-ol in 40 ml CH$_2$Cl$_2$ was added over a time period of 15 min. The reaction mixture was stirred at 37° C. for 3 h, cooled to room temperature treated with 80 ml water and solid NaCl. After extraction and phase separation the water phases were extracted 3 times with 70 ml CH$_2$Cl$_2$. The combined organic phase was dried over Na$_2$SO$_4$, concentrated to a volume of 70 ml, treated with 75 ml toluene and concentrated to a volume of ca. 100 ml. After 3 d at 0° C. the suspension was concentrated to 50 ml and filtered to yield 9.2 g crude product as white crystals. Chromatographic purification on SiO$_2$ (CH$_2$Cl$_2$/tert.-butylmethyl ether (tBME)=19/1) yielded 7.2 g (87.1%) product as white powder.

MS (ISP): 398 (8, [M+Na]$^+$), 376 (100, [M+H]$^+$), 358 (12).

M.p. 155.5–156.2° C.

Example G.2

As in example 7.1. but instead of chromatographic purification, the crude product is purified by crystallization (dissolving in methanol, afterwards exchange methanol by toluene).

Example H

Preparation of 4-(2-hydroxy-ethylsulfanyl)-phenol

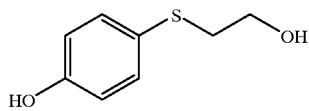

A solution of 5.0 g (35.7 mmol) 4-mercaptophenol in 50 ml methyl alcohol was treated at −5° C. dropwise over a period of 30 min with 39.2 ml (39.2 mmol) aqueous NaOH 1N and stirred 1 h at −5° C. Afterwards a solution of 5.2 ml (39.2 mmol) 2-bromo ethanol in 16.5 ml methyl alcohol was added at −5° C. dropwise over a period of 15 min. The reaction mixture was stirred for 21 h at room temperature, concentrated and the residue treated with 10 ml water and 30 ml tBME. After extraction and phase separation, the organic phase was washed with 20 ml saturated NaHCO$_3$ and 20 ml brine. The combined organic phases were dried over Na$_2$SO$_4$ and the solvent was removed under reduced pressure to yield 6.03 g crude product. The crude product was dissolved in 18 ml tBME at 40° C. and subsequently treated dropwise with 25 ml hexane. The so formed suspension was stirred 16 h at room temperature and 1 h at 4° C. The crystals were separated on a filter funnel and washed with 5 ml hexane (4° C.) to yield 4.8 g (77.7%) product as white crystals.

MS (ISN): 229 (100, [M+OAc]$^-$), 169 (29, [M−H]$^-$).

M.p.: 71.5–72.0° C.

Example I

Preparation of 4-(2-hydroxy-ethansulfonyl)-phenol

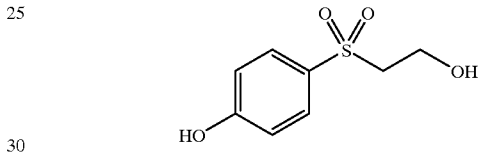

A solution of 5.0 g (28.5 mmol) 4-(2-hydroxy-ethylsulfanyl)-phenol in 25 ml methyl alcohol was treated at 10° C. in parts over 20 min with 26.3 g (42.8 mmol) oxone ®. The suspension was stirred at room temperature (exothermic reaction) for 2 h, filtrated and the filtrate treated with 1 ml aqueous sodium hydrogen sulfite solution (38–40%). The pH of the reaction mixture was adjusted to 7 with 2 ml aqueous NaOH (28%), the suspension filtrated and the filtrate evaporated. The residue was treated with 20 ml toluene and subsequent the solvent evaporated. This procedure was repeated two times to yield 6.81 g crude product as white crystals.

MS (EI): 202 (9, [M]), 174 (13), 157 (30), 109 (32),94 (100)

M.p.: 125.9–127.6° C.

Example J

Preparation of 4-(2-chloro-ethansulfonyl)-phenol

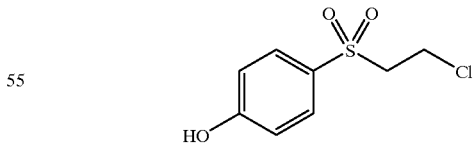

A solution of 6.81 g crude 4-(2-hydroxy-ethansulfonyl)-phenol in 35 ml CH$_2$Cl$_2$ was treated at room temperature with 5.3 ml (65.9 mmol) pyridine. To the reaction mixture was added at 0° C. dropwise over 15 min a solution of 4.2 ml (57.1 mmol) thionyl chloride in 10 ml CH$_2$Cl$_2$. After 65 h at room temperature the reaction mixture was treated with 35 ml brine, extracted and the organic phases were washed twice with total 100 ml aqueous half saturated NaCl solution. The combined organic phases were dried over $Na_2SO_4$ and the solvent was removed under reduced pressure to yield 6.77 g crude product. The crude product was dissolved in 2.5 ml $CH_2Cl_2$ and 25 ml toluene, stirred 24 h at 50° C., 24 h at room temperature and 48 h at 0° C. The so formed suspension was filtered to yield 5.44 g (86.5% over 2 steps) product as white crystals.

MS (EI): 220 (17, [M]), 157 (100), 109 (18), 94 (17), 93 (60), 65 (41).

M.p.: 72.5–73.5° C.

Tablet Formulation Wet Granulation

| Ingredients | mg/tablet | | | |
|---|---|---|---|---|
| 1. Active compound | 5 | 25 | 100 | 500 |
| 2. Lactose Anhydrous DTG | 125 | 105 | 30 | 150 |
| 3. Sta-Rx 1500 | 6 | 6 | 6 | 30 |
| 4. Microcrystalline Cellulose | 30 | 30 | 30 | 150 |
| 5. Magnesium Stearate | 1 | 1 | 1 | 1 |
| TOTAL | 167 | 167 | 167 | 831 |

Manufacturing Procedure

1. Mix Items 1, 2, 3 and 4 and granulate with purified water.
2. Dry the granulation at 50° C.
3. Pass the granulation through suitable milling equipment.
4. Add Item 5 and mix for three minutes; compress on a suitable press.

Capsule Formulation

| Ingredients | mg/capsule | | | |
|---|---|---|---|---|
| 1. Active compound | 5 | 25 | 100 | 500 |
| 2. Hydrous Lactose | 159 | 123 | 148 | — |
| 3. Corn Starch | 25 | 35 | 40 | 70 |
| 4. Talc | 10 | 15 | 10 | 25 |
| 5. Magnesium Stearate | 1 | 2 | 2 | 5 |
| TOTAL | 200 | 200 | 300 | 600 |

Manufacturing Procedure

1. Mix Items 1, 2, and 3 in a suitable mixer for 30 minutes.
2. Add Items 4 and 5 and mix for 3 minutes.
3. Fill into a suitable capsule.

Tablet Formulation Wet Granulation

| Ingredients | mg/tablet | | | |
|---|---|---|---|---|
| 1. Active compound | 5 | 25 | 100 | 500 |
| 2. Lactose Anhydrous | 125 | 105 | 30 | 150 |
| 3. Sta-Rx 1500 | 6 | 6 | 6 | 30 |
| 4. Microcrystalline Cellulose | 30 | 30 | 30 | 150 |
| 5. Magnesium Stearate | 1 | 2 | 2 | 5 |
| TOTAL | 167 | 167 | 167 | 835 |

Manufacturing Procedure

1. Mix Items 1, 2, 3 and 4 and granulate with purified water.
2. Dry the granulation at 50° C.
3. Pass the granulation through suitable milling equipment.
4. Add Item 5 and mix for three minutes; compress on a suitable press.

What is claimed is:

1. A compound of formula I

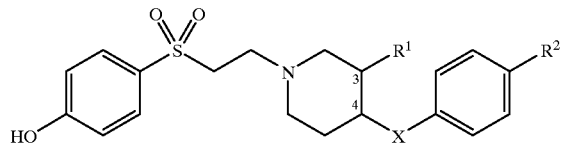

wherein $R^1$ signifies hydrogen or hydroxy;

$R^2$ signifies hydrogen or methyl; and

X signifies —O— or —$CH_2$— and their pharmaceutically acceptable acid addition salts.

2. A compound of claim 1 which is cis at positions 3 and 4.

3. A compound of claim 1 wherein X is —O—.

4. A compound of claim 3 which is 4-[2-(4-p-tolyloxy-piperidin-1-yl)-ethanesulfonyl]-phenol.

5. A compound of claim 1 wherein X is —$CH_2$—.

6. A compound of claim 5 which is 4[-2-(4-benzyl-piperidine-1-yl)-ethanesulfonyl]-phenol.

7. A compound of claim 5 wherein $R^1$ is hydroxy.

8. A compound of claim 7 wherein $R^2$ is hydrogen.

9. A compound of claim 8 which is (+)(3R,4R)-4-benzyl-1-[2-(4-hydroxy-benzenesulfonyl)-ethyl]-piperidin-3-ol.

10. A compound of claim 8 which is (−)(3S,4S)-4-benzyl-1-[2-(4-hydroxy-benzenesulfonyl)-ethyl]-piperidin-3-ol.

11. A compound of claim 8 which is (3RS,4RS)-4-benzyl-1-[2-(4-hydroxy-benzenesulfonyl)-ethyl]-piperidin-3-ol.

12. A compound of claim 7 wherein $R^2$ is methyl.

13. A compound of claim 12 which is (+)(cis)-1-[2-(4-hydroxy-benzenesulfonyl)-ethyl]-4-(4-methyl-benzyl)-piperidin-3-ol.

14. A compound of claim 12 which is (−)(cis)-1-[2-(4-hydroxy-benzenesulfonyl)-ethyl]-4-(4-methyl-benzyl)-piperidin-3-ol.

15. A compound of claim 12 which is (3RS,4RS)-1-[2-(4-hydroxy-benzenesulfonyl)-ethyl]-4-(4-methyl-benzyl)-piperidin-3-ol.

16. A pharmaceutical composition comprising the compound of claim 1 and a pharmaceutically acceptable carrier.

* * * * *